US010779760B2

United States Patent
Lee et al.

(10) Patent No.: US 10,779,760 B2
(45) Date of Patent: *Sep. 22, 2020

(54) DECEPTION DETECTION SYSTEM AND METHOD

(71) Applicant: NURALOGIX CORPORATION, Toronto (CA)

(72) Inventors: Kang Lee, Toronto (CA); Pu Zheng, Toronto (CA)

(73) Assignee: NuraLogix Corporation, Toronto (CA)

( * ) Notice: Subject to any disclaimer, the term of this patent is extended or adjusted under 35 U.S.C. 154(b) by 0 days.

This patent is subject to a terminal disclaimer.

(21) Appl. No.: 16/507,565

(22) Filed: Jul. 10, 2019

(65) Prior Publication Data

US 2020/0022631 A1 Jan. 23, 2020

Related U.S. Application Data

(63) Continuation of application No. 16/076,492, filed as application No. PCT/CA2017/050141 on Feb. 8, 2017, now Pat. No. 10,390,747.

(Continued)

(51) Int. Cl.
*G06K 9/00* (2006.01)
*A61B 5/16* (2006.01)
(Continued)

(52) U.S. Cl.
CPC ............ *A61B 5/164* (2013.01); *A61B 5/0077* (2013.01); *A61B 5/02* (2013.01); *A61B 5/026* (2013.01); *A61B 5/0261* (2013.01); *A61B 5/1455* (2013.01); *A61B 5/14546* (2013.01); *A61B 5/16* (2013.01); *A61B 5/165* (2013.01); *A61B 5/7267* (2013.01); *A61B 5/742* (2013.01); *A61B 5/7405* (2013.01); *G06K 9/00221* (2013.01); *G06K 9/00302* (2013.01); *G06K 9/00315* (2013.01); *G06K 9/4661* (2013.01); *G06N 3/02* (2013.01);
(Continued)

(58) Field of Classification Search
CPC ......... A61B 5/02; A61B 5/026; A61B 5/0261; A61B 5/16; A61B 5/164; A61B 5/165; G06K 9/00221; G06K 9/00302; G06K 9/00315
See application file for complete search history.

(56) References Cited

U.S. PATENT DOCUMENTS 8,219,438 B1 * 7/2012 Moon ................ G06Q 30/0201
705/7.29
10,390,747 B2 * 8/2019 Lee ........................... G06N 3/02
(Continued)

*Primary Examiner* — Andrew W Bee
(74) *Attorney, Agent, or Firm* — Bhole IP Law; Anil Bhole; Marc Lampert

(57) ABSTRACT

A system for detecting deception is provided. The system comprises a camera, an image processing unit, and a notification device. The camera is configured to capture an image sequence of a person of interest. The image processing unit is trained to determine a set of bitplanes of a plurality of images in the captured image sequence that represent the hemoglobin concentration (HC) changes of the person, and to detect the person's invisible emotional states based on HC changes. The image processing unit is trained using a training set comprising a set of subjects for which emotional state is known. The notification device provides a notification of at least one of the person's detected invisible emotional states.

18 Claims, 14 Drawing Sheets

Related U.S. Application Data

(60) Provisional application No. 62/292,577, filed on Feb. 8, 2016.

(51) Int. Cl.

| | | |
|---|---|---|
| *A61B 5/026* | (2006.01) | |
| *A61B 5/02* | (2006.01) | |
| *A61B 5/00* | (2006.01) | |
| *A61B 5/145* | (2006.01) | |
| *G08B 5/38* | (2006.01) | |
| *G06K 9/46* | (2006.01) | |
| *G06N 3/08* | (2006.01) | |
| *G06N 3/04* | (2006.01) | |
| *G06N 3/02* | (2006.01) | |
| *G06N 20/00* | (2019.01) | |
| *A61B 5/1455* | (2006.01) | |
| *G10L 15/22* | (2006.01) | |
| *G10L 25/63* | (2013.01) | |
| *A61B 5/021* | (2006.01) | |
| *A61B 5/0402* | (2006.01) | |
| *A61B 5/08* | (2006.01) | |
| *A61B 5/103* | (2006.01) | |

(52) U.S. Cl.
CPC ............ *G06N 3/0445* (2013.01); *G06N 3/08* (2013.01); *G06N 20/00* (2019.01); *G08B 5/38* (2013.01); *G10L 15/22* (2013.01); *G10L 25/63* (2013.01); *A61B 5/021* (2013.01); *A61B 5/0402* (2013.01); *A61B 5/08* (2013.01); *A61B 5/1032* (2013.01); *A61B 5/443* (2013.01); *A61B 2576/00* (2013.01); *G06K 2009/4666* (2013.01)

(56) References Cited

U.S. PATENT DOCUMENTS

| | | | |
|---|---|---|---|
| 2005/0054935 A1* | 3/2005 | Rice ................. | A61B 5/0261 600/473 |
| 2011/0212717 A1* | 9/2011 | Rhoads ............. | G06F 16/58 455/420 |
| 2014/0107439 A1* | 4/2014 | Atsumori ......... | A61B 5/165 600/322 |
| 2016/0098592 A1* | 4/2016 | Lee .................. | G06F 19/321 434/236 |
| 2019/0041984 A1* | 2/2019 | Lee .................. | A61B 5/0077 |
| 2019/0043069 A1* | 2/2019 | Lee .................. | A61B 5/145 |
| 2019/0046099 A1* | 2/2019 | Lee .................. | A61B 5/024 |
| 2020/0050837 A1* | 2/2020 | Lee .................. | G06K 9/6278 |

\* cited by examiner

DECEPTION DETECTION SYSTEM AND METHOD

TECHNICAL FIELD

The following relates generally to security and more specifically to an image-capture based system and method for detecting deception.

BACKGROUND

Security has been considered a relatively-high concern for a number of recent years. Of particular interest is security afforded to checkpoints, such as border crossings, airport security checkpoints, sensitive building entrances, etc. While it is desirable to provide very thorough security, there is a balance between the security afforded and the comprehensive costs associated therewith. There are a few main costs for providing security at such checkpoints: manpower, efficiency, and, as a result, use.

In order to understand the threat that a person poses, the person can be searched in an attempt to identify the threat, or the person can be interviewed. This latter option is generally more rapid and less invasive, leading to a lower level of dissatisfaction in users/customers. Security staff at security checkpoints is trained to identify possible deception based on visual cues and audio cues. A person, however, can condition themselves to reduce the human-perceptible signs of deception, such as twitches, fidgeting, wavering in the voice, a break in eye contact, etc. As a result, while staff training can lead to the detection of some deception, it is unlikely to lead to the detection of deception for more egregious cases.

The detection of deception and hidden emotions generally is of interest in other circumstances, such as during the interrogation of a suspect or a potential witness of a crime, or the surveillance of a person of interest. In such cases, it can be helpful to identify hidden or otherwise obscured emotions that can provide insight into the veracity of answers provided, the anxiousness/discomfort of a person, etc.

SUMMARY

In one aspect, a system for detecting deception for the security screening of a person of interest by an attendant, is provided, the system comprising: a camera configured to capture an image sequence of the person of interest; a processing unit trained to determine a set of bitplanes of a plurality of images in the captured image sequence that represent the hemoglobin concentration (HC) changes of the person, to detect the person's invisible emotional states based on HC changes, and to output the detected invisible emotional states, the processing unit being trained using a training set comprising HC changes of subjects with known emotional states; and, a notification device for providing a notification of at least one of the person's detected invisible emotional states to the attendant based on the output of the processing unit.

In another aspect, a method for detecting deception for the security screening of a person of interest by an attendant, is provided, the method comprising: capturing, by a camera, an image sequence of the person of interest; determining, by a processing unit, a set of bitplanes of a plurality of images in the captured image sequence that represent the hemoglobin concentration (HC) changes of the person, detecting the person's invisible emotional states based on HC changes, and outputting the detected invisible emotional states, the processing unit being trained using a training set comprising HC changes of subjects with known emotional states; and, providing a notification, by a notification device, of at least one of the person's detected invisible emotional states to the attendant based on the output of the processing unit.

BRIEF DESCRIPTION OF THE DRAWINGS

The features of the invention will become more apparent in the following detailed description in which reference is made to the appended drawings wherein.

DETAILED DESCRIPTION

Figure 1:
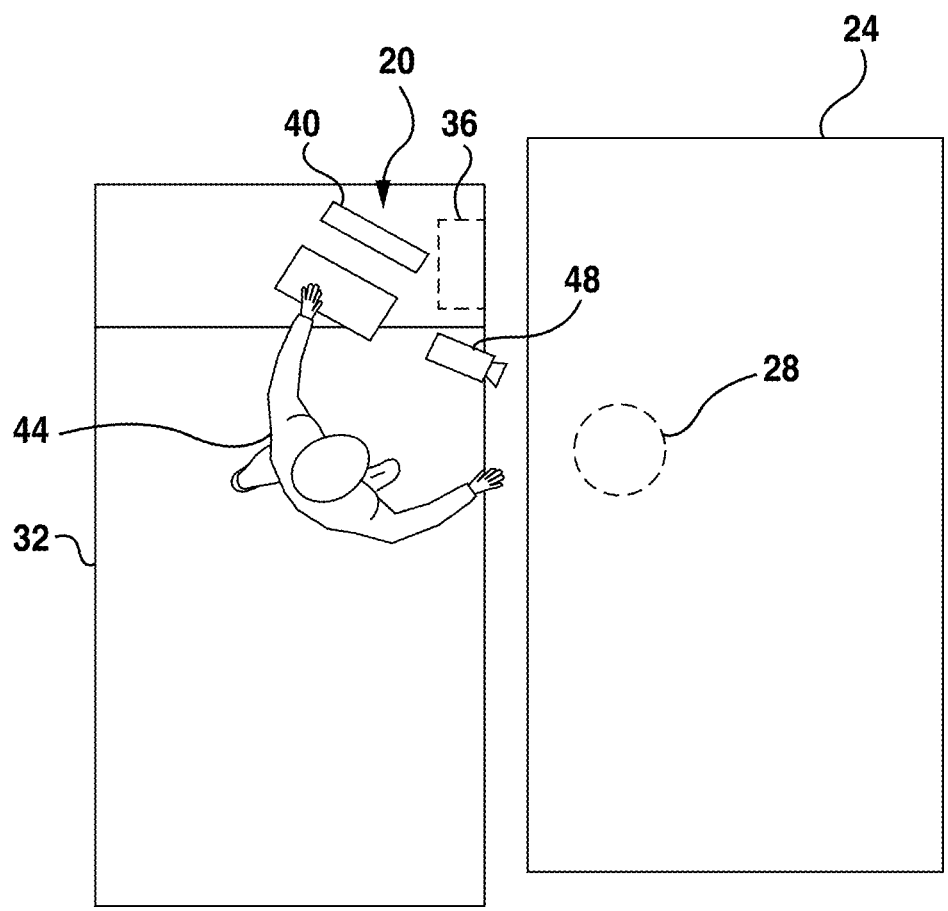
FIG. 1 is a top-down section view of a system for detecting deception employed at a border security checkpoint in accordance with an embodiment.

Embodiments will now be described with reference to the figures. For simplicity and clarity of illustration, where considered appropriate, reference numerals may be repeated among the Figures to indicate corresponding or analogous elements. In addition, numerous specific details are set forth in order to provide a thorough understanding of the embodiments described herein. However, it will be understood by those of ordinary skill in the art that the embodiments described herein may be practiced without these specific details. In other instances, well-known methods, procedures and components have not been described in detail so as not to obscure the embodiments described herein. Also, the description is not to be considered as limiting the scope of the embodiments described herein.

Various terms used throughout the present description may be read and understood as follows, unless the context indicates otherwise: "or" as used throughout is inclusive, as though written "and/or"; singular articles and pronouns as used throughout include their plural forms, and vice versa; similarly, gendered pronouns include their counterpart pronouns so that pronouns should not be understood as limiting anything described herein to use, implementation, performance, etc. by a single gender; "exemplary" should be understood as "illustrative" or "exemplifying" and not necessarily as "preferred" over other embodiments. Further definitions for terms may be set out herein; these may apply to prior and subsequent instances of those terms, as will be understood from a reading of the present description.

Any module, unit, component, server, computer, terminal, engine or device exemplified herein that executes instructions may include or otherwise have access to computer readable media such as storage media, computer storage media, or data storage devices (removable and/or non-removable) such as, for example, magnetic disks, optical disks, or tape. Computer storage media may include volatile and non-volatile, removable and non-removable media implemented in any method or technology for storage of information, such as computer readable instructions, data structures, program modules, or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by an application, module, or both. Any such computer storage media may be part of the device or accessible or connectable thereto. Further, unless the context clearly indicates otherwise, any processor or controller set out herein may be implemented as a singular processor or as a plurality of processors. The plurality of processors may be arrayed or distributed, and any processing function referred to herein may be carried out by one or by a plurality of processors, even though a single processor may be exemplified. Any method, application or module herein described may be implemented using computer readable/executable instructions that may be stored or otherwise held by such computer readable media and executed by the one or more processors.

The following relates generally to a system for detecting deception and a method therefor. A specific embodiment relates to an image-capture based system and method for detecting deception at a security checkpoint, and specifically the invisible emotional state of an individual captured in a series of images or a video. The system provides a remote and non-invasive approach by which to detect deception with a high confidence.

It can be desirable to determine the emotional state of a person to detect deception and/or discomfort. For example, a person passing a security checkpoint may be unusually uncomfortable with the experience, or may hide or alter the truth when answering a question of security checkpoint staff or a question posed in a checkpoint machine. It can be relatively easy to control one's visible emotional state, but very difficult to mask physiological changes corresponding to emotional state changes. The detected invisible emotion can be used by security checkpoint staff to make decisions regarding the further investigation of a person passing through.

FIG. 1 shows a system 20 for detecting deception at a border security checkpoint in accordance with an embodiment. A vehicle 24 is shown having a driver 28 positioned inside in a driver's seat. The vehicle 24 is pulled up to a border security checkpoint station 32. The system 20 is deployed inside the border security checkpoint station 32, and comprises a computer system 36, a display 40 which is shown as angled to be visible only to a border security guard 44 and not to the driver 28, and a camera 48 coupled to the computer system 36 via a wired or wireless communication medium, such as Ethernet, Universal Serial Bus ("USB"), IEEE 802.11 ("Wi-Fi"), Bluetooth, etc.

The camera 48 is configured to capture image sequences of particular body parts of the driver 28. Typically, the driver's 28 face will be captured. The camera 38 can be any suitable visible light camera type for capturing an image sequence of a consumer's face, such as, for example, a CMOS or CCD camera. The camera 48 can be configured with lenses to enable image capture from a wider angle, and the computer system 34 can be configured to transform the image sequences to compensate for any distortion introduced by the lenses.

Figure 3:
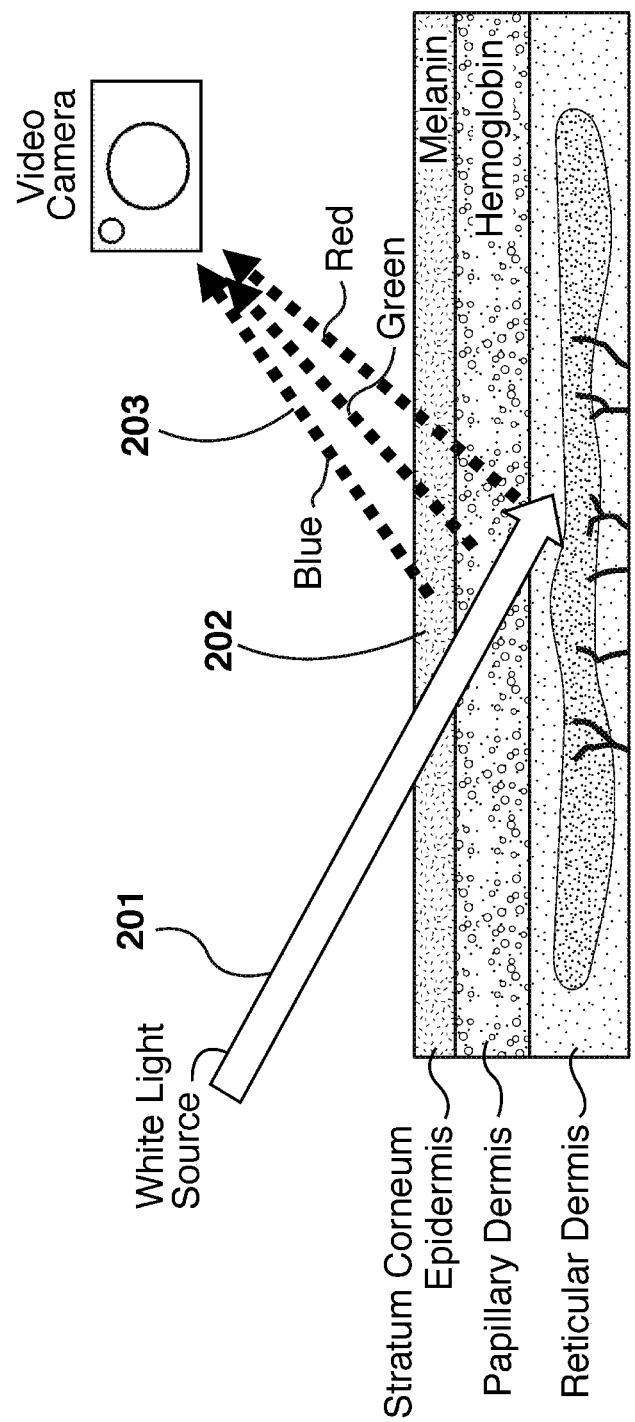
FIG. 3 illustrates re-emission of light from skin epidermal and subdermal layers.
Figure 4:
FIG. 4 is a set of surface and corresponding transdermal images illustrating change in hemoglobin concentration associated with invisible emotion for a particular human subject at a particular point in time.
Figure 5:
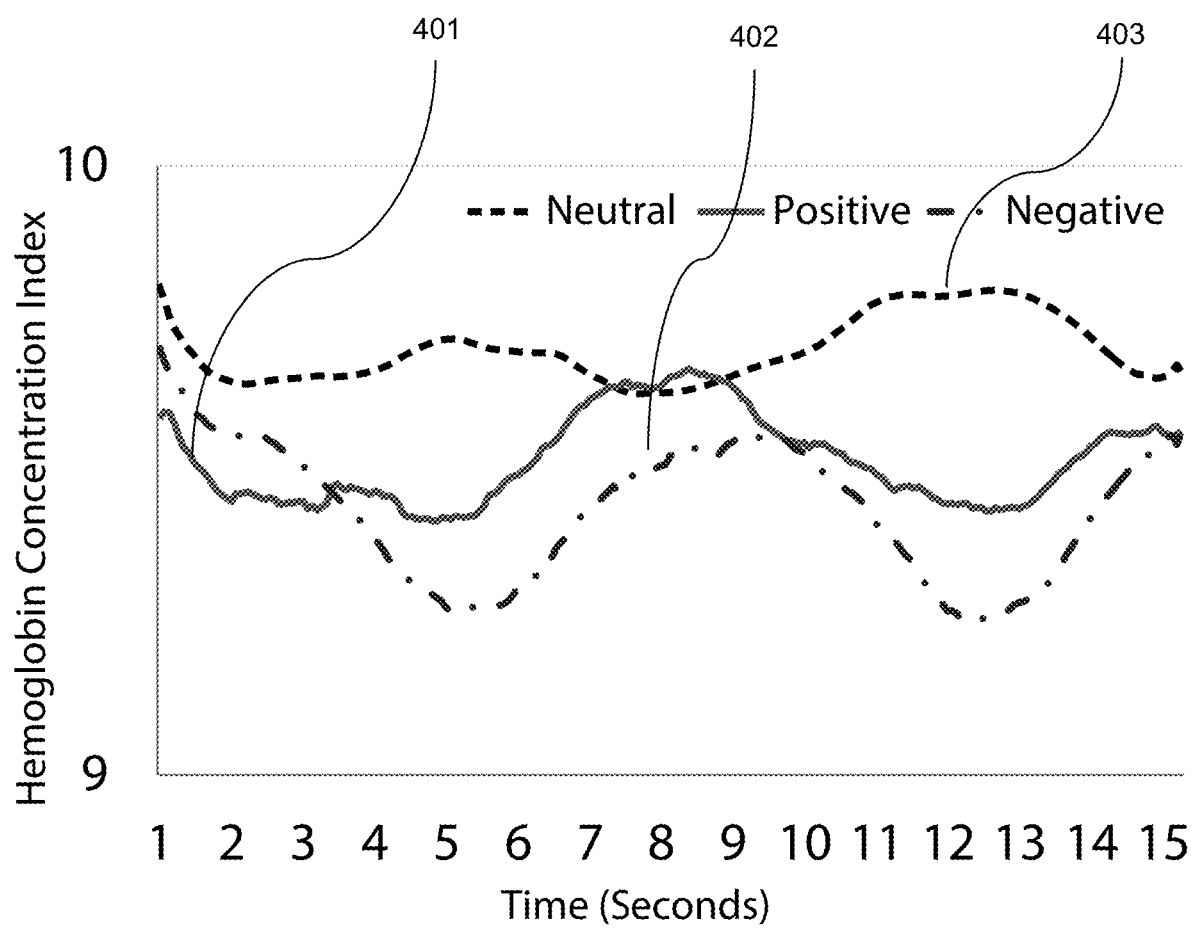
FIG. 5 is a plot illustrating hemoglobin concentration changes for the forehead of a subject who experiences positive, negative, and neutral emotional states as a function of time (seconds)

Hemoglobin concentration (HC) can be isolated from raw images taken from the camera 38, and spatial-temporal changes in HC can be correlated to human emotion. Referring now to FIG. 3, a diagram illustrating the re-emission of light from skin is shown. Light (201) travels beneath the skin (202), and re-emits (203) after travelling through different skin tissues. The re-emitted light (203) may then be captured by optical cameras. The dominant chromophores affecting the re-emitted light are melanin and hemoglobin. Since melanin and hemoglobin have different color signatures, it has been found that it is possible to obtain images mainly reflecting HC under the epidermis as shown in FIG. 4.

The system 20 implements a two-step method to generate rules suitable to output an estimated statistical probability that a human subject's emotional state belongs to one of a plurality of emotions, and a normalized intensity measure of such emotional state given a video sequence of any subject. The emotions detectable by the system correspond to those for which the system is trained.

Figure 2:
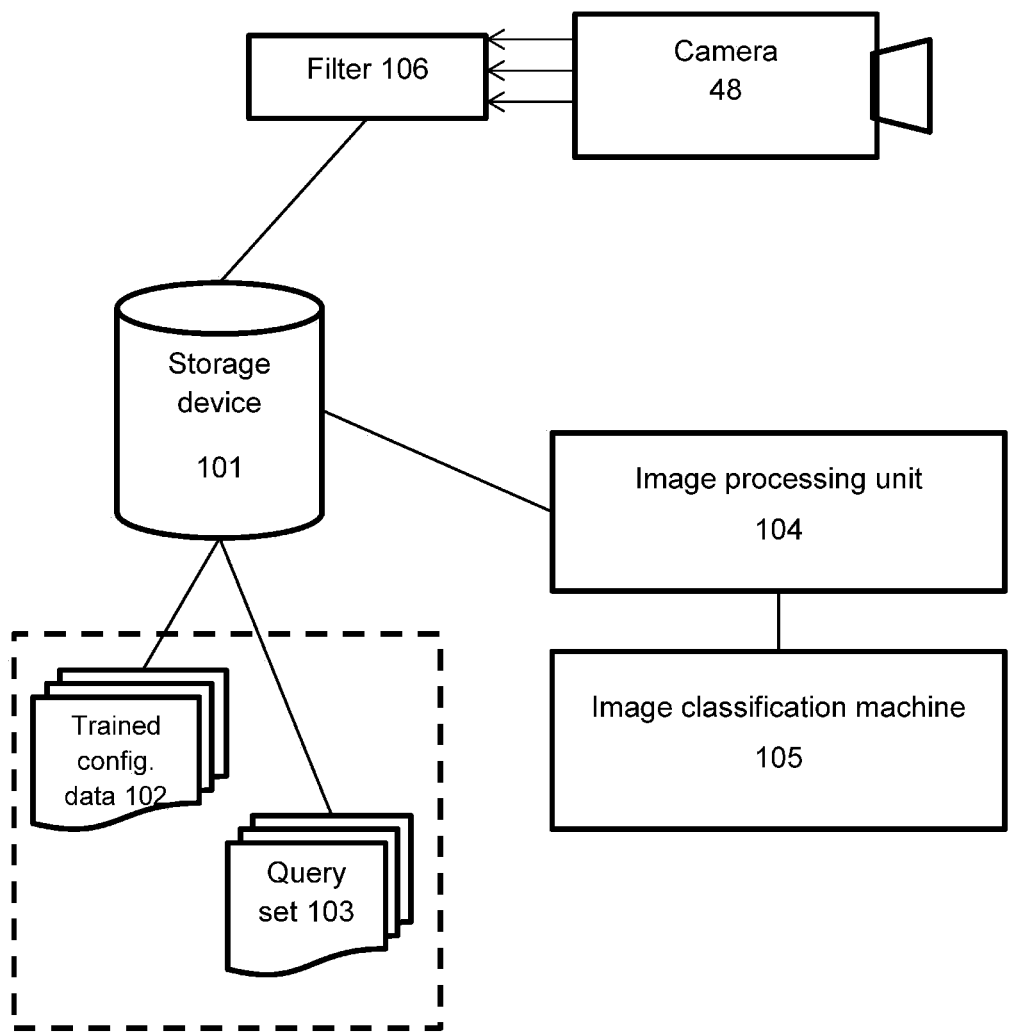
FIG. 2 is an block diagram of various components of the system for deception detection of FIG. 1.

Referring now to FIG. 2, various components of the system 20 for deception detection at a security checkpoint are shown in isolation. The computer system 34 comprises an image processing unit 104, an image filter 106, an image classification machine 105, and a storage device 101. A processor of the computer system 34 retrieves computer-readable instructions from the storage device 101 and executes them to implement the image processing unit 104, the image filter 106, and the image classification machine 105, The image classification machine 105 is configured with training configuration data 102 derived from another computer system trained using a training set of images and is operable to perform classification for a query set of images 103 which are generated from images captured by the camera 38, processed by the image filter 106, and stored on the storage device 102.

The sympathetic and parasympathetic nervous systems are responsive to emotion. It has been found that an individual's blood flow is controlled by the sympathetic and parasympathetic nervous system, which is beyond the conscious control of the vast majority of individuals. Thus, an individual's internally experienced emotion can be readily detected by monitoring their blood flow. Internal emotion systems prepare humans to cope with different situations in the environment by adjusting the activations of the autonomic nervous system (ANS); the sympathetic and parasympathetic nervous systems play different roles in emotion regulation with the former regulating up fight-flight reactions whereas the latter serves to regulate down the stress reactions. Basic emotions have distinct ANS signatures. Blood flow in most parts of the face such as eyelids, cheeks and chin is predominantly controlled by the sympathetic vasodilator neurons, whereas blood flowing in the nose and ears is mainly controlled by the sympathetic vasoconstrictor neurons; in contrast, the blood flow in the forehead region is innervated by both sympathetic and parasympathetic vasodilators. Thus, different internal emotional states have differential spatial and temporal activation patterns on the different parts of the face. By obtaining hemoglobin data from the system, facial hemoglobin concentration (HC) changes in various specific facial areas may be extracted. These multidimensional and dynamic arrays of data from an individual are then compared to computational models based on normative data to be discussed in more detail below. From such comparisons, reliable statistically based inferences about an individual's internal emotional states may be made. Because facial hemoglobin activities controlled by the ANS are not readily subject to conscious controls, such activities provide an excellent window into an individual's genuine innermost emotions.

Figure 8:
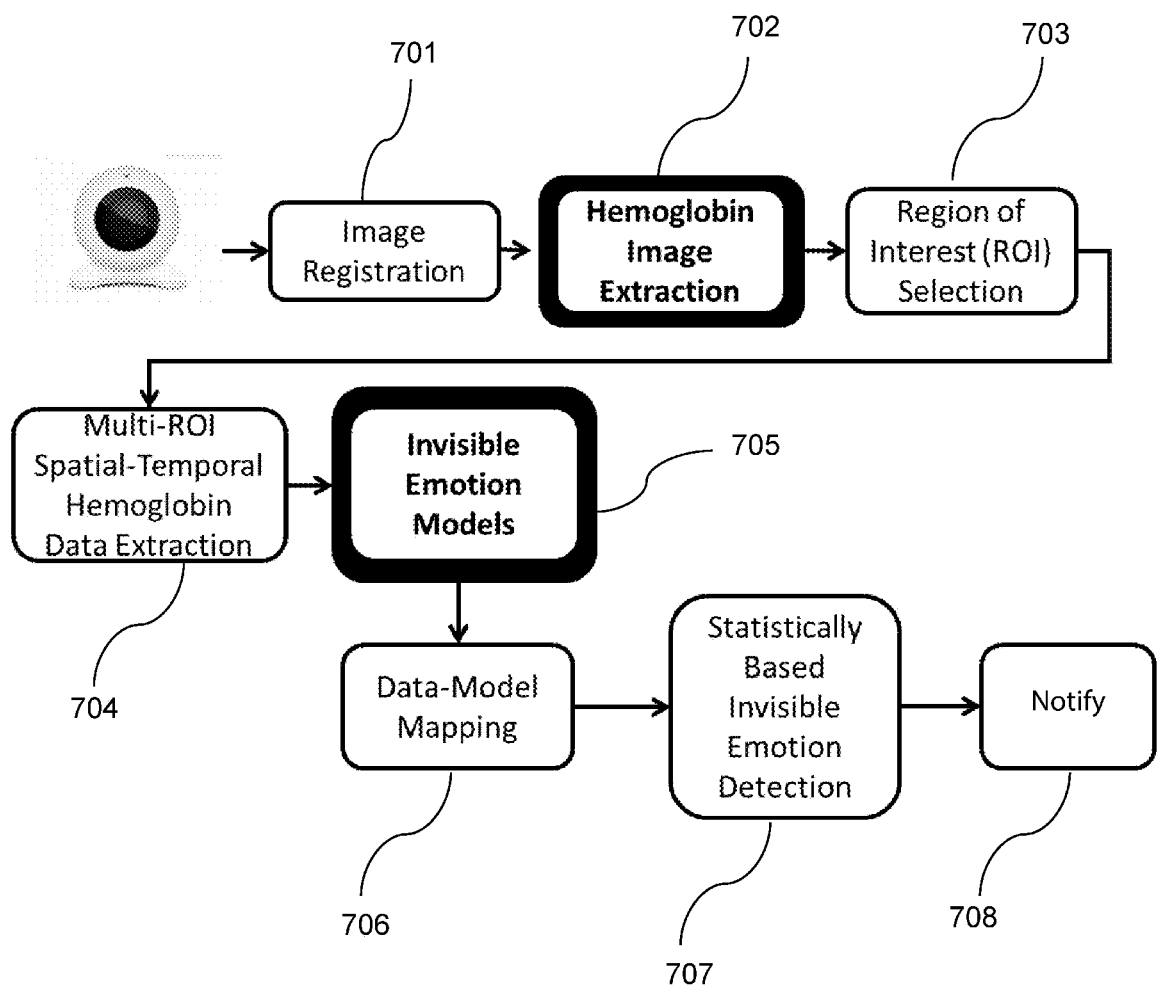
FIG. 8 is a flowchart illustrating a fully automated transdermal optical imaging and invisible emotion detection system.
Figure 12:
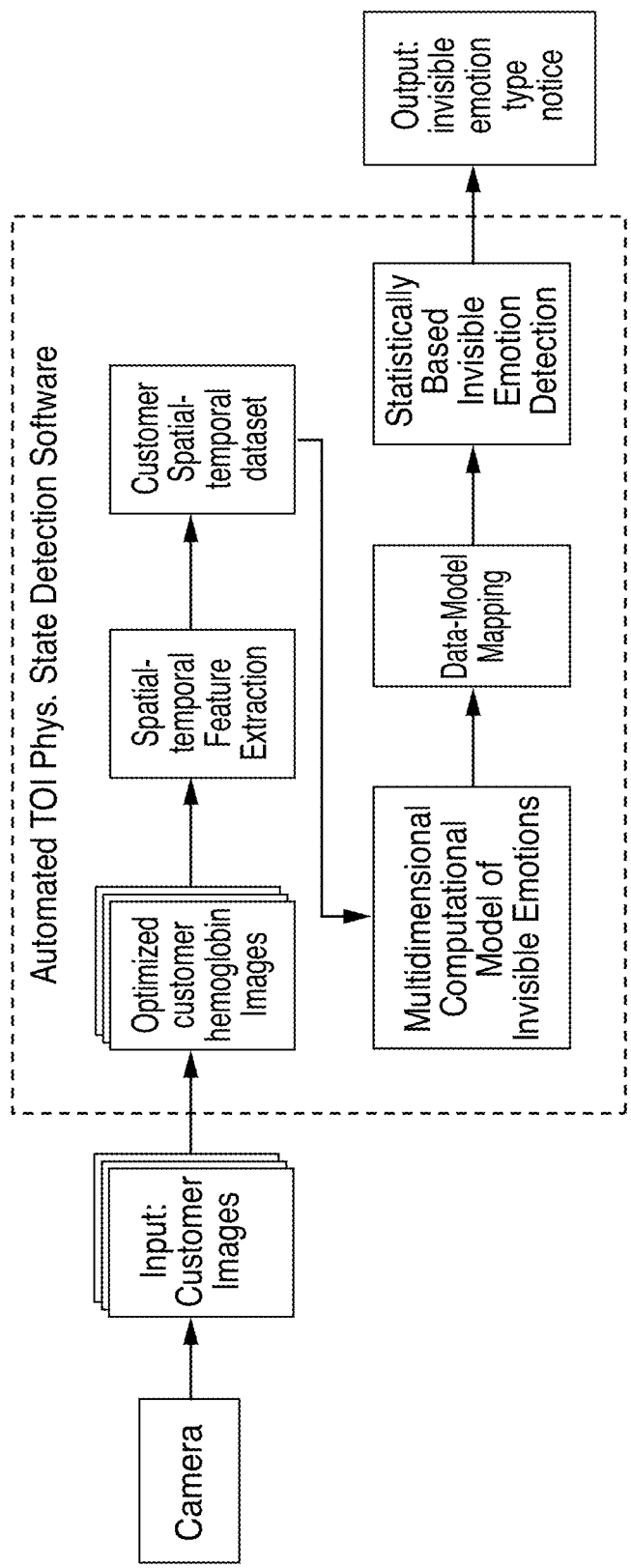
FIG. 12 is an illustration of an automated invisible emotion detection system.

Referring now to FIG. 8, a flowchart illustrating the method of invisible emotion detection performed by the system 20 is shown. The system 20 performs image registration 701 to register the input of a video/image sequence captured of a subject with an unknown emotional state, hemoglobin image extraction 702, ROI selection 703, multi-ROI spatial-temporal hemoglobin data extraction 704, invisible emotion model 705 application, data mapping 706 for mapping the hemoglobin patterns of change, emotion detection 707, and notification 708. FIG. 12 depicts another such illustration of automated invisible emotion detection system.

The image processing unit obtains each captured image or video stream from each camera and performs operations upon the image to generate a corresponding optimized HC image of the subject. The image processing unit isolates HC in the captured video sequence. In an exemplary embodiment, the images of the subject's faces are taken at 30 frames per second using the camera. It will be appreciated that this process may be performed with alternative digital cameras and lighting conditions.

Isolating HC is accomplished by analyzing bitplanes in the video sequence to determine and isolate a set of the bitplanes that provide high signal to noise ratio (SNR) and, therefore, optimize signal differentiation between different emotional states on the facial epidermis (or any part of the human epidermis). The determination of high SNR bitplanes is made with reference to a first training set of images constituting the captured video sequence, coupled with EKG, pneumatic respiration, blood pressure, laser Doppler data from the human subjects from which the training set is obtained. The EKG and pneumatic respiration data are used to remove cardiac, respiratory, and blood pressure data in the HC data to prevent such activities from masking the more-subtle emotion-related signals in the HC data. The second step comprises training a machine to build a computational model for a particular emotion using spatial-temporal signal patterns of epidermal HC changes in regions of interest ("ROIs") extracted from the optimized "bitplaned" images of a large sample of human subjects.

For training, video images of test subjects exposed to stimuli known to elicit specific emotional responses are captured. Responses may be grouped broadly (neutral, positive, negative) or more specifically (distressed, happy, anxious, sad, frustrated, intrigued, joy, disgust, angry, surprised, contempt, etc.). In further embodiments, levels within each emotional state may be captured. Preferably, subjects are instructed not to express any emotions on the face so that the emotional reactions measured are invisible emotions and isolated to changes in HC. To ensure subjects do not "leak" emotions in facial expressions, the surface image sequences may be analyzed with a facial emotional expression detection program. EKG, pneumatic respiratory, blood pressure, and laser Doppler data may further be collected using an EKG machine, a pneumatic respiration machine, a continuous blood pressure machine, and a laser Doppler machine and provides additional information to reduce noise from the bitplane analysis, as follows.

ROIs for emotional detection (e.g., forehead, nose, and cheeks) are defined manually or automatically for the video images. These ROIs are preferably selected on the basis of knowledge in the art in respect of ROIs for which HC is particularly indicative of emotional state. Using the native images that consist of all bitplanes of all three R, G, B channels, signals that change over a particular time period (e.g., 10 seconds) on each of the ROIs in a particular emotional state (e.g., positive) are extracted. The process may be repeated with other emotional states (e.g., negative or neutral). The EKG and pneumatic respiration data may be used to filter out the cardiac, respirator, and blood pressure signals on the image sequences to prevent non-emotional systemic HC signals from masking true emotion-related HC signals. Fast Fourier transformation (FFT) may be used on the EKG, respiration, and blood pressure data to obtain the peek frequencies of EKG, respiration, and blood pressure, and then notch filers may be used to remove HC activities on the ROIs with temporal frequencies centering around these frequencies. Independent component analysis (ICA) may be used to accomplish the same goal.

Figure 10:
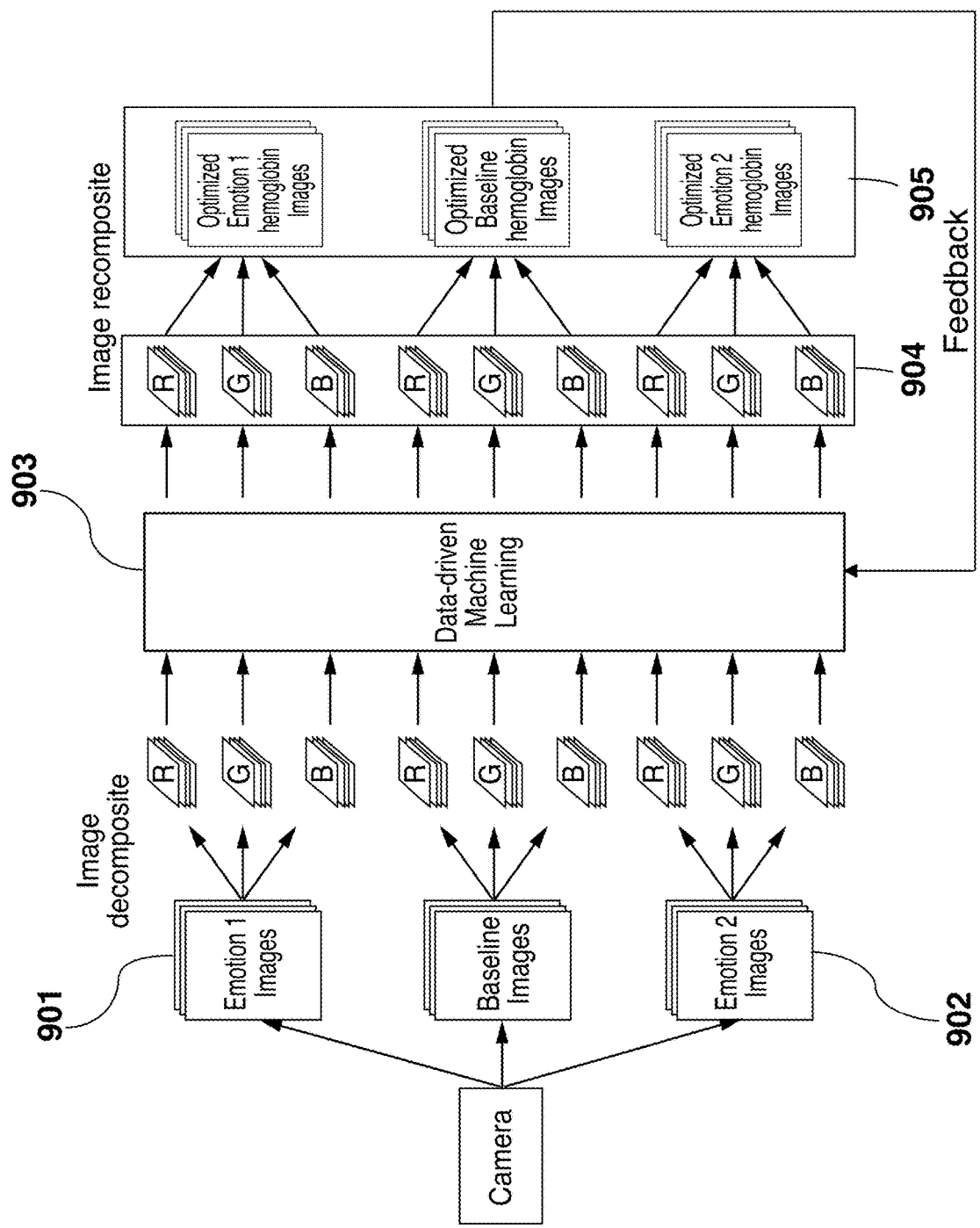
FIG. 10 is an illustration of a data-driven machine learning system for optimized hemoglobin image composition.

Referring now to FIG. 10 an illustration of data-driven machine learning for optimized hemoglobin image composition is shown. Using the filtered signals from the ROIs of two or more than two emotional states 901 and 902, machine learning 903 is employed to systematically identify bitplanes 904 that will significantly increase the signal differentiation between the different emotional state and bitplanes that will contribute nothing or decrease the signal differentiation between different emotional states. After discarding the latter, the remaining bitplane images 905 that optimally differentiate the emotional states of interest are obtained. To further improve SNR, the result can be fed back to the machine learning 903 process repeatedly until the SNR reaches an optimal asymptote.

The machine learning process involves manipulating the bitplane vectors (e.g., 8×8×8, 16×16×16) using image subtraction and addition to maximize the signal differences in all ROIs between different emotional states over the time period for a portion (e.g., 70%, 80%, 90%) of the subject data and validate on the remaining subject data. The addition or subtraction is performed in a pixel-wise manner. An existing machine learning algorithm, the Long Short Term Memory (LSTM) neural network, or a suitable alternative thereto is used to efficiently and obtain information about the improvement of differentiation between emotional states in terms of accuracy, which bitplane(s) contributes the best information, and which does not in terms of feature selection. The Long Short Term Memory (LSTM) neural network or another suitable machine training approach (such as deep learning) allows us to perform group feature selections and classifications. The LSTM machine learning algorithm is discussed in more detail below. From this process, the set of bitplanes to be isolated from image sequences to reflect temporal changes in HC is obtained. An image filter is configured to isolate the identified bitplanes in subsequent steps described below.

The image classification machine 105 is configured with trained configuration data 102 from a training computer system previously trained with a training set of images captured using the above approach. In this manner, the image classification machine 105 benefits from the training performed by the training computer system. The image classification machine 104 classifies the captured image as corresponding to an emotional state. In the second step, using a new training set of subject emotional data derived from the optimized biplane images provided above, machine learning is employed again to build computational models for emotional states of interests (e.g., positive, negative, and neural).

Figure 11:
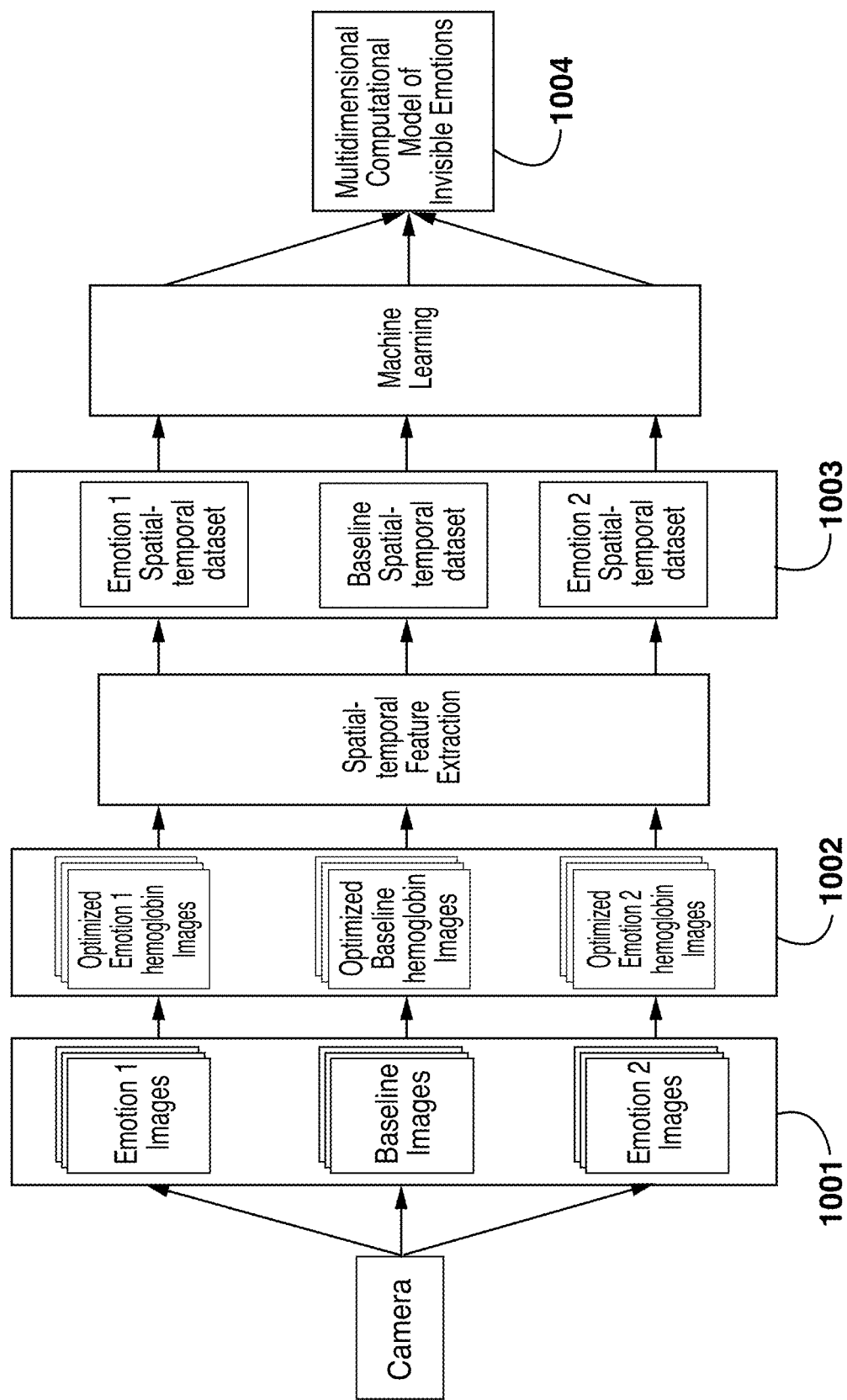
FIG. 11 is an illustration of a data-driven machine learning system for multidimensional invisible emotion model building.

Referring now to FIG. 11, an illustration of data-driven machine learning for multidimensional invisible emotion model building is shown. To create such models, a second set of training subjects (preferably, a new multi-ethnic group of training subjects with different skin types) is recruited, and image sequences 1001 are obtained when they are exposed to stimuli eliciting known emotional response (e.g., positive, negative, neutral). An exemplary set of stimuli is the International Affective Picture System, which has been commonly used to induce emotions and other well established emotion-evoking paradigms. The image filter is applied to the image sequences 1001 to generate high HC SNR image sequences. The stimuli could further comprise non-visual aspects, such as auditory, taste, smell, touch or other sensory stimuli, or combinations thereof.

Using this new training set of subject emotional data 1003 derived from the bitplane filtered images 1002, machine learning is used again to build computational models for emotional states of interests (e.g., positive, negative, and neural) 1003. Note that the emotional state of interest used to identify remaining bitplane filtered images that optimally differentiate the emotional states of interest and the state used to build computational models for emotional states of interests must be the same. For different emotional states of interests, the former must be repeated before the latter commences.

The machine learning process again involves a portion of the subject data (e.g., 70%, 80%, 90% of the subject data) and uses the remaining subject data to validate the model. This second machine learning process thus produces separate multidimensional (spatial and temporal) computational models of trained emotions 1004.

To build different emotional models, facial HC change data on each pixel of each subject's face image is extracted (from Step 1) as a function of time when the subject is viewing a particular emotion-evoking stimulus. To increase SNR, the subject's face is divided into a plurality of ROIs according to their differential underlying ANS regulatory mechanisms mentioned above, and the data in each ROI is averaged.

Figure 6:
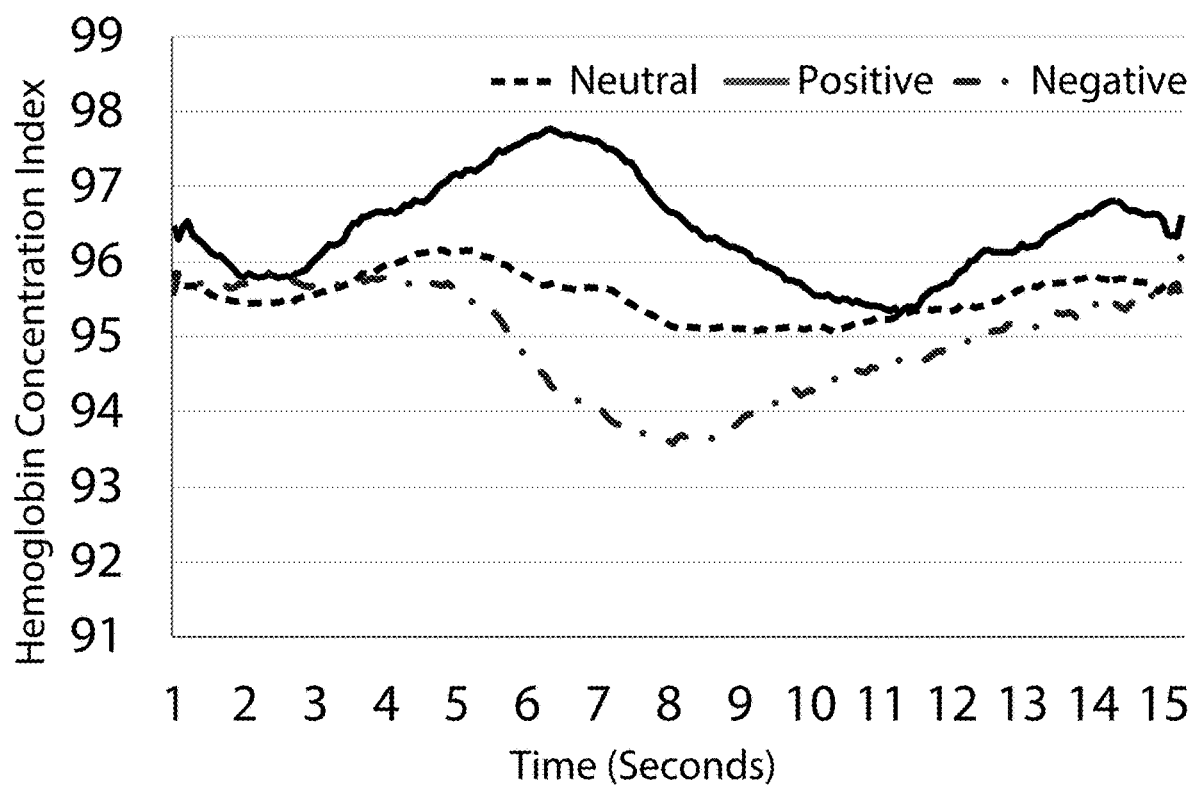
FIG. 6 is a plot illustrating hemoglobin concentration changes for the nose of a subject who experiences positive, negative, and neutral emotional states as a function of time (seconds)
Figure 7:
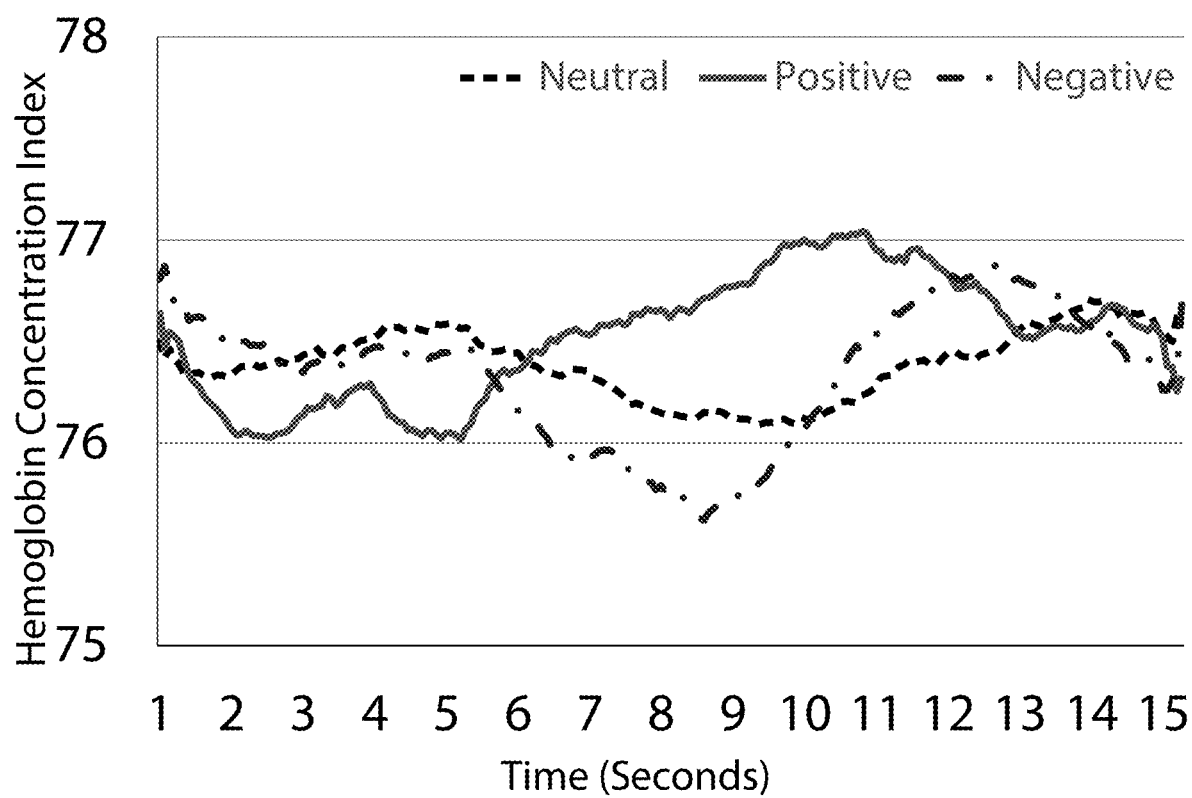
FIG. 7 is a plot illustrating hemoglobin concentration changes for the cheek of a subject who experiences positive, negative, and neutral emotional states as a function of time (seconds)

Referring now to FIG. 4, a plot illustrating differences in hemoglobin distribution for the forehead of a subject is shown. Though neither human nor computer-based facial expression detection system may detect any facial expression differences, transdermal images show a marked difference in hemoglobin distribution between positive 401, negative 402 and neutral 403 conditions. Differences in hemoglobin distribution for the nose and cheek of a subject may be seen in FIG. 6 and FIG. 7 respectively.

The Long Short Term Memory (LSTM) neural network, or a suitable alternative such as non-linear Support Vector Machine, and deep learning may again be used to assess the existence of common spatial-temporal patterns of hemoglobin changes across subjects. The Long Short Term Memory (LSTM) neural network or an alternative is trained on the transdermal data from a portion of the subjects (e.g., 70%, 80%, 90%) to obtain a multi-dimensional computational model for each of the three invisible emotional categories. The models are then tested on the data from the remaining training subjects.

These models form the basis for the trained configuration data 102.

Following these steps, it is now possible to obtain a video sequence from the camera 48 of a person in the vehicle 24 and apply the HC extracted from the selected biplanes to the computational models for emotional states of interest. The output will be a notification corresponding to (1) an estimated statistical probability that the subject's emotional state belongs to one of the trained emotions, and (2) a normalized intensity measure of such emotional state. For long running video streams when emotional states change and intensity fluctuates, changes of the probability estimation and intensity scores over time relying on HC data based on a moving time window (e.g., 10 seconds) may be reported. It will be appreciated that the confidence level of categorization may be less than 100%.

Two example implementations for (1) obtaining information about the improvement of differentiation between emotional states in terms of accuracy, (2) identifying which bitplane contributes the best information and which does not in terms of feature selection, and (3) assessing the existence of common spatial-temporal patterns of hemoglobin changes across subjects will now be described in more detail. One such implementation is a recurrent neural network.

Figure 13:
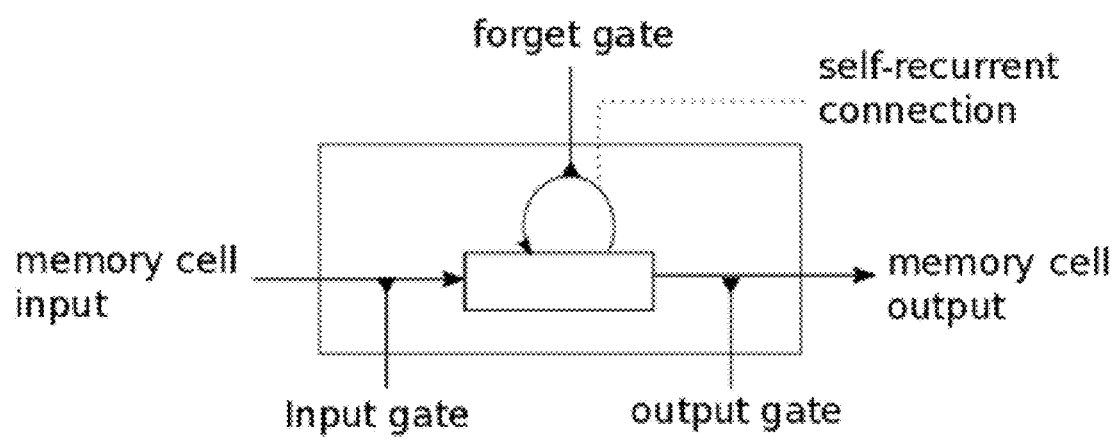
FIG. 13 is a memory cell.

One recurrent neural network is known as the Long Short Term Memory (LSTM) neural network, which is a category of neural network model specified for sequential data analysis and prediction. The LSTM neural network comprises at least three layers of cells. The first layer is an input layer, which accepts the input data. The second (and perhaps additional) layer is a hidden layer, which is composed of memory cells (see FIG. 13). The final layer is output layer, which generates the output value based on the hidden layer using Logistic Regression.

Each memory cell, as illustrated, comprises four main elements: an input gate, a neuron with a self-recurrent connection (a connection to itself), a forget gate and an output gate. The self-recurrent connection has a weight of 1.0 and ensures that, barring any outside interference, the state of a memory cell can remain constant from one time step to another. The gates serve to modulate the interactions between the memory cell itself and its environment. The input gate permits or prevents an incoming signal to alter the state of the memory cell. On the other hand, the output gate can permit or prevent the state of the memory cell to have an effect on other neurons. Finally, the forget gate can modulate the memory cell's self-recurrent connection, permitting the cell to remember or forget its previous state, as needed.

The equations below describe how a layer of memory cells is updated at every time step t. In these equations:

$x_t$ is the input array to the memory cell layer at time t. In our application, this is the blood flow signal at all ROIs $$\vec{x}_t = [x_{1t}, x_{2t}, \ldots, x_{nt}]$$

$W_i$, $W_f$, $W_c$, $W_o$, $U_i$, $U_f$, $U_c$, $U_o$ and $V_o$ are weight matrices; and $b_i$, $b_f$, $b_c$ and $b_o$ are bias vectors First, we compute the values for $i_t$, the input gate, and $\tilde{C}_t$ the candidate value for the states of the memory cells at time t:

$$i_t = \sigma(W_i x_t + U_i h_{t-1} + b_i)$$

$$\tilde{C}_t = \tanh(W_c x_t + U_c h_{t-1} + b_c)$$

Second, we compute the value for $f_t$, the activation of the memory cells' forget gates at time t:

$$f_t = \sigma(W_f x_t + U_f h_{t-1} + b_f)$$

Given the value of the input gate activation $i_t$, the forget gate activation $f_t$ and the candidate state value $\tilde{C}_t$, we can compute $C_t$ the memory cells' new state at time t:

$$C_t = i_t * \tilde{C}_t + f_t * C_{t-1}$$

With the new state of the memory cells, we can compute the value of their output gates and, subsequently, their outputs:

$$o_t = \sigma(W_o x_t + U_o h_{t-1} + V_o C_t + b_o)$$

$$h_t = o_t * \tanh(C_t)$$

Based on the model of memory cells, for the blood flow distribution at each time step, we can calculate the output from memory cells. Thus, from an input sequence $x_0, x_1, x_2, \ldots, x_n$, the memory cells in the LSTM layer will produce a representation sequence $h_0, h_1, h_2, \ldots, h_n$.

The goal is to classify the sequence into different conditions. The Logistic Regression output layer generates the probability of each condition based on the representation sequence from the LSTM hidden layer. The vector of the probabilities at time step t can be calculated by:

$$p_t = \text{softmax}(W_{output} h_t + b_{output})$$

where $W_{output}$ is the weight matrix from the hidden layer to the output layer, and $b_{output}$ is the bias vector of the output layer. The condition with the maximum accumulated probability will be the predicted condition of this sequence.

The computer system 36 registers the image streams captured from the camera 48 and makes a determination of the invisible emotion detected using the process described above. The detected invisible emotion is then registered with a time, date, license plate, and the video stream captured by the camera 48. The computer system 34 can be configured to discard the image sequences upon detecting the invisible emotion. The computer system 34 then notifies the border security guard 44 of the detected invisible emotion and its intensity.

Figure 9:
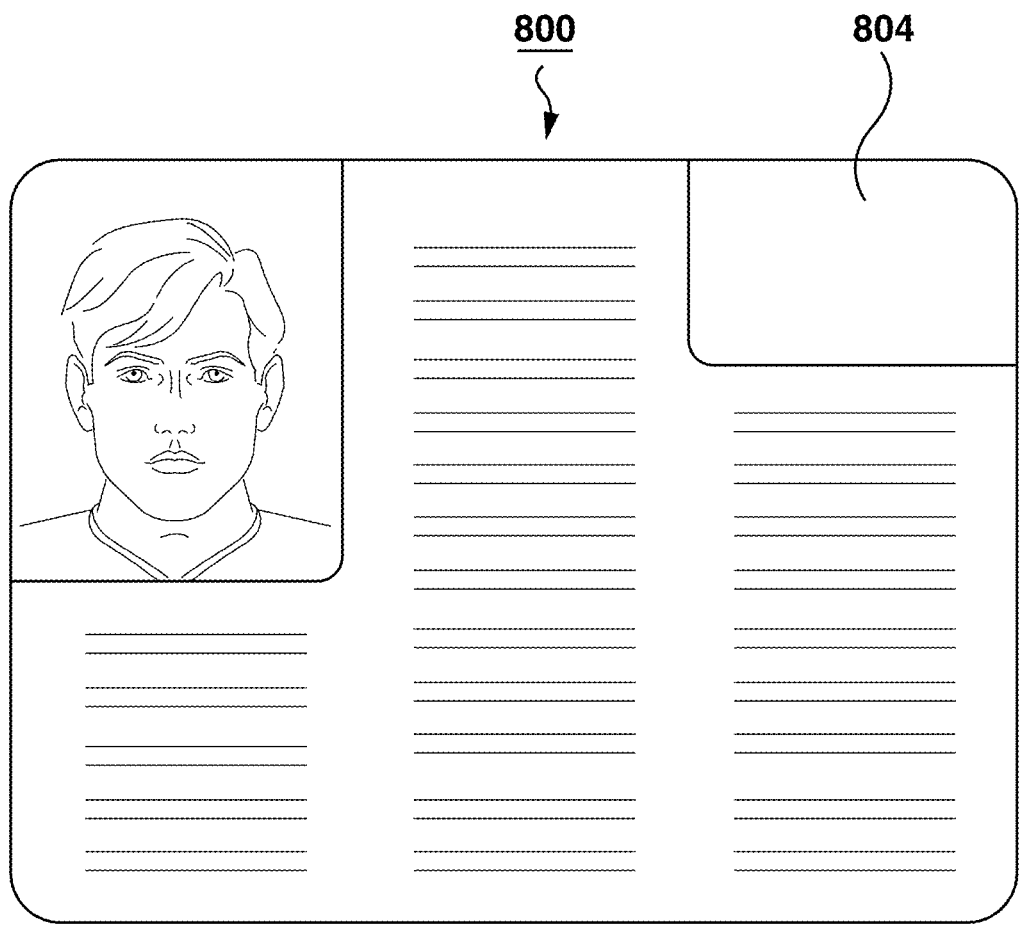
FIG. 9 is an exemplary screen presented to the border security guard by the computer system via the display of FIG. 1.

Referring now to FIG. 9, an exemplary screen 800 presented on the display 40 by the computer system 36. The screen 800 presents a photo of the driver 28 retrieved from a database using the driver's passport identification number, as well as various data related to the driver 28. In addition, the screen 800 presents a notification area 804 that comprises a color. The color shown corresponds to the detected invisible emotion and its intensity. For a strong, positive invisible emotion, a green field is presented. When a neutral emotion is detected, a white field is presented. If a negative invisible emotion is detected, a red field is presented. The intensity of the color corresponds to the intensity of the detected invisible emotion. In the case of a negative detected invisible emotion, the red field presented in the notification area 804 may flash to draw the attention of the border security guard 44. As the display 40 is only visible to the border security guard 44, the driver 28 will be unaware of the detected invisible emotion.

The border security guard 44 can then use the presented notification to detect when the driver 28 may be ill at ease, potentially related to discomfort with a question or with a deceptive answer provided by the driver 28 in response to a question.

In other embodiments, the computer system 36 can be configured to generate and present a graph of the detected invisible emotions so that the border security guard 44 can review past detected invisible emotions in case the guard's attention was diverted.

In another embodiment, the computer system 36 can be configured to present text on the display 40 to further notify a person of the detected invisible emotion. In another embodiment, a separate device such as an LED that is only visible to guard 44 can be employed in a position in the field of view of the border security guard. In a further embodiment, the computer system 36 can notify a person of the detected invisible emotion via an audible noise transmitted to an earpiece worn by the person. In yet another embodiment, haptic feedback can be provided to a person through a wearable device with a haptic engine and that is in communication with the computer system 36. In still yet another embodiment, a notification can be made on a surface of a pair of glasses worn by a person that is only visible to the wearer.

The computer system 36 is configured in another embodiment to calculate a probability of deception by the person being questioned based on the emotions detected and their intensity, and present this information graphically and/or textually to the border security guard.

Other methods of representing the detected invisible emotion will be apparent to a person skilled in the art.

Figure 14:
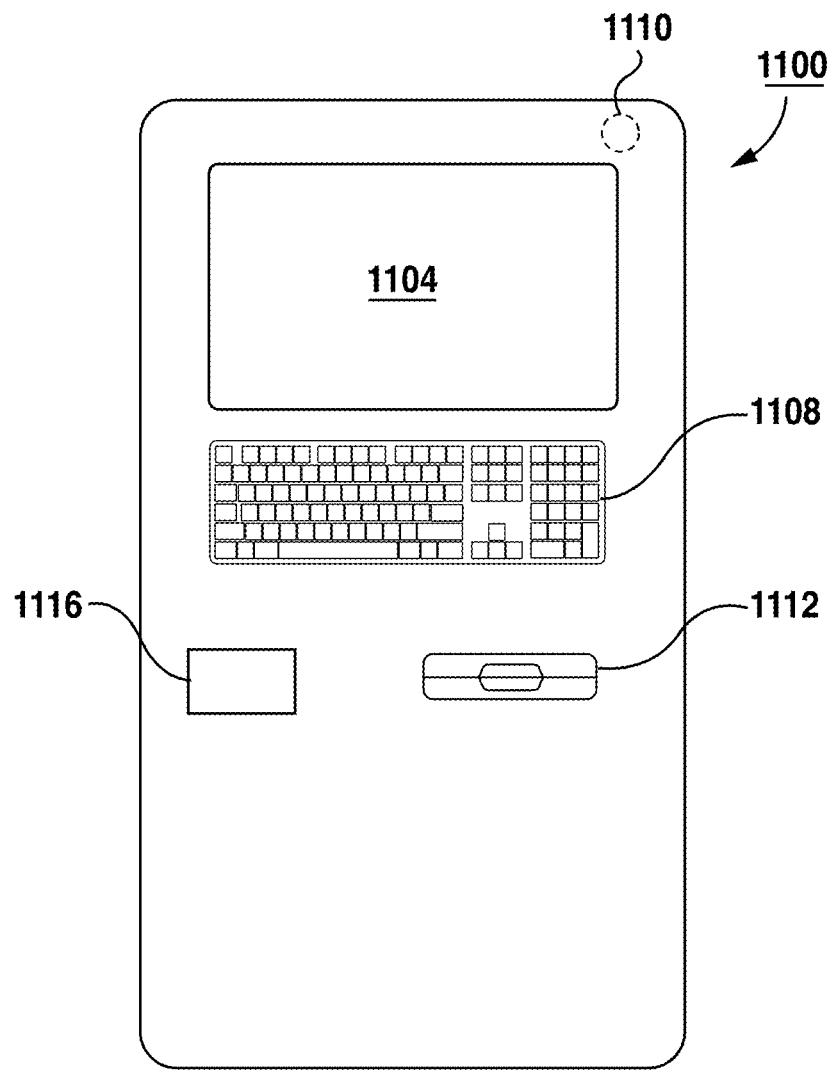
FIG. 14 is a kiosk for presenting a questionnaire, and having a camera for detecting deception in accordance with another embodiment.

In another embodiment shown in FIG. 14, a kiosk 1100 enables an at least partially automatic screening process at a security checkpoint. The kiosk 1100 may be, for example, provided in airport border control stations. The kiosk 1100 has a touchscreen 1104 for presenting a series of questions in an interview via a display. Feedback can be received via the touchscreen 1104, a keyboard 1108, a microphone (not shown), etc. The kiosk 1100 may also be equipped with a hidden camera 1110 that is configured to capture image sequences of the face of a person using the kiosk 1100. Alternatively, or in addition, a camera may be provided for a physical area corresponding to several kiosks and capable of monitoring a plurality of persons. A passport scanner 1112 scans passports inserted therein.

The captured image sequences can be analyzed by a processor within the kiosk 1100 (or sent to another computing device for analysis) to detect invisible human emotions, and thus deception, during the questionnaire. The kiosk 1100 may then prepare a summary of the interview responses, together with the invisible human emotions, and probability of deception, detected during the interview such that they are correlated to the questions posed. In one configuration, the kiosk 1100 may notify security personnel of a condition, such as a detected invisible human emotion and corresponding probability of deception at a particular point in the interview. In another configuration, the kiosk can print an interview summary receipt via a printout slot having an identification number or barcode corresponding with the results that are communicated to and stored in a central database. The interviewed person can then take the interview summary receipt to security staff for review. In this configuration, the security staff can scan in the barcode or type in the identification number from the interview summary receipt and review the results retrieved from the central database.

In other embodiments, the camera capturing image sequences of a person's face can be separate from the computing device that performs the deception detection. The image sequences can be communicated to the computing device performing the detection via a wired or wireless computer communications network, or via removable storage. For example, a smartphone can capture image sequences and audio and transmit them over a Wi-Fi network to a computer system that is configured to perform the invisible human emotion detection.

While the above-described embodiments are described in relation to checkpoint security, it will be appreciated that the above method and system can be adapted for use with other types of security. For example, similar systems and methods can be used in airport security, building ingress security, border/customs checkpoints, police investigations, military investigations, consular interviews, spying operations, court depositions, etc. Further, the system can be configured to monitor a person of interest during other activities via one or more visible or invisible cameras to detect invisible human emotions and thus deception. In various applications, the system can be used in connection with a question/answer methodology, to detect deception associated with specific information, or with a candid capture methodology, to detect deceptive intent generally.

Although the invention has been described with reference to certain specific embodiments, various modifications thereof will be apparent to those skilled in the art without departing from the spirit and scope of the invention as outlined in the claims appended hereto. The entire disclosures of all references recited above are incorporated herein by reference.

We claim:

1. A system for detecting an emotional state of a person of interest, the system comprising a processing unit and a storage device, the processing unit configurable to:
   receive an image sequence captured of the person of interest;
   determine hemoglobin concentration (HC) changes of the person of interest from the image sequence;
   determine an emotional state associated with the person of interest using a trained classification machine learning model, the trained classification machine learning model receiving the HC changes as input, the training set for the trained classification machine learning model comprising previously determined HC changes from images of subjects with known emotional states; and
   output the determined emotional state.

2. The system of claim 1, wherein the emotional state comprises one of positive, negative, and neutral.

3. The system of claim 2, wherein the trained classification machine learning model further determines an associated intensity measure for the positive emotional state and the negative emotional state, and wherein the associated intensity is outputted with the respective determined emotional state.

4. The system of claim 3, wherein the processing unit is further configurable to determine a probability of deception by the person being questioned based on the determined emotional state and the associated intensity as input to a trained deception machine learning model, and to output the determined probability of deception.

5. The system of claim 4, wherein the probability of deception is determined periodically as new images in the image sequence are received.

6. The system of claim 4, wherein the HC changes are determined using an HC machine learning model trained with a HC training set, bit values from a set of bitplanes in the captured image sequence that represent HC changes are fed as input to the HC machine learning model, the training set for the HC machine learning model comprising bit values from each bitplane of images captured from persons for which HC is known.

7. The system of claim 6, wherein the set of bitplanes being those that are determined to approximately maximize a signal-to-noise ratio (SNR).

8. The system of claim 6, wherein the HC machine learning model comprises a Long Short Term Memory (LSTM) neural network.

9. The system of claim 4, wherein outputting the determined emotional state and outputting the probability of deception collectively comprise communicating the determined emotional state and the probability of deception to a display for presentation to an attendant.

10. A method for detecting an emotional state of a person of interest, the method executed on a processing unit, the method comprising:
    receiving an image sequence captured of the person of interest;
    determining hemoglobin concentration (HC) changes of the person of interest from the image sequence;
    determining an emotional state associated with the person of interest using a trained classification machine learning model, the trained classification machine learning model receiving the HC changes as input, the training set for the trained classification machine learning model comprising previously determined HC changes from images of subjects with known emotional states; and
    outputting the determined emotional state.

11. The method of claim 10, wherein the emotional state comprises one of positive, negative, and neutral.

12. The method of claim 11, wherein the trained classification machine learning model further determines an associated intensity measure for the positive emotional state and the negative emotional state, and wherein the associated intensity is outputted with the respective determined emotional state.

13. The method of claim 12, further comprising determining a probability of deception by the person being questioned based on the determined emotional state and the associated intensity as input to a trained deception machine learning model, and outputting the determined probability of deception.

14. The method of claim 13, wherein the probability of deception is determined periodically as new images in the image sequence are received.

15. The method of claim 13, wherein the HC changes are determined using an HC machine learning model trained with a HC training set, bit values from a set of bitplanes in the captured image sequence that represent HC changes are fed as input to the HC machine learning model, the training set for the HC machine learning model comprising bit values from each bitplane of images captured from persons for which HC is known.

16. The method of claim 15, wherein the set of bitplanes being those that are determined to approximately maximize a signal-to-noise ratio (SNR).

17. The method of claim 15, wherein the HC machine learning model comprises a Long Short Term Memory (LSTM) neural network.

18. The method of claim 13, wherein outputting the determined emotional state and outputting the probability of deception collectively comprise displaying the determined emotional state and the probability of deception to an attendant.

* * * * *